United States Patent [19]

Elving

[11] Patent Number: 4,985,353

[45] Date of Patent: Jan. 15, 1991

[54] METHOD FOR THE DIAGNOSIS OF WHOOPING-COUGH AND A TEST KIT FOR CARRYING THE METHOD INTO EFFECT

[75] Inventor: Hans B. O. Elving, Linköping, Sweden

[73] Assignee: Trion Forskning-Och Utvecklings Aktiebolag, Sollentuna, Sweden

[21] Appl. No.: 375,024

[22] PCT Filed: Dec. 10, 1987

[86] PCT No.: PCT/SE87/00588

§ 371 Date: Aug. 15, 1989

§ 102(e) Date: Aug. 15, 1989

[87] PCT Pub. No.: WO88/04693

PCT Pub. Date: Jun. 30, 1988

[30] Foreign Application Priority Data

Dec. 16, 1986 [SE] Sweden ................ 8605389-9

[51] Int. Cl.$^5$ ............... G01N 33/569; C12Q 1/02; C12Q 1/04
[52] U.S. Cl. ............................ 435/7; 435/4; 435/29; 435/34; 435/810; 436/805
[58] Field of Search ............... 435/34, 35, 810, 822, 435/7, 29; 436/63, 805; 424/92

[56] References Cited

U.S. PATENT DOCUMENTS 4,652,521  3/1987  Confer et al. .................. 435/34

OTHER PUBLICATIONS

Karlsson, J. O. G. et al; Chemical Abstracts, vol. 103; p. 468; (Life Sci. 1985).

*Primary Examiner*—Esther L. Kepplinger
*Assistant Examiner*—Daniel R. Passeri
*Attorney, Agent, or Firm*—Bacon & Thomas

[57] ABSTRACT

A method for the diagnosis of whooping-cough is described. The method is carried out such that a sample of body fluid from a patient is incubated with at least a part of a pertussis toxin-sensitive, chromatophore containing fish-scale during a predetermined suitable period of time, that the fish-scale colour then is subjected to a first visual inspection, optionally by means of a microscope, that a substance inducing a colour change in the fish-scales is added, that the fish-scale colour then is subjected to a second visual inspection, optionally by means of the microscope and that the fish-scale colour first observed is compared with the subsequently observed fish-scale colour, the absence of a colour change, or a slight colour change, indicating the presence of pertussis toxin in the body fluid sample.

A test kit for carrying the method into effect is described as well.

7 Claims, No Drawings

METHOD FOR THE DIAGNOSIS OF WHOOPING-COUGH AND A TEST KIT FOR CARRYING THE METHOD INTO EFFECT

The present invention relates to a method for the diagnosis of whooping-cough and to a test kit for carrying the method into effect. The method according to the invention makes it possible directly to detect the presence of pertussis toxin produced by the whooping-cough bacterium (*Bordetella pertussis*) in samples of body fluid (sputum, nasopharyngeal secretion, saliva or blood).

PRIOR ART

In practical application, two different methods are being used at present for the diagnosis of whooping-cough in patients suspected of being infected with the whooping-cough bacterium, viz. a culture method and a serological method.

CULTURE METHOD

Conventional hospital technique for the diagnosis of whooping-cough is based on the culturing of whole whooping-cough bacteria from nasopharyngeal, sputum or saliva samples from a patient suspected of being infected. The culture can then be used for detecting the bacterium. Samples for culturing are not taken until whooping-cough is suspected in a patient, usually after 3-4 weeks when the symptom begins to distinguish from an ordinary cold, and then it is frequently too late for a reliable result by culturing the sample because but a few whooping-cough bacteria, or none at all, remain in the sample. The culturing method is time-consuming, and furthermore the whooping-cough bacterium is difficult to culture and sensitive to the culturing conditions and to the transport of the sample to the laboratory. The sensitivity of this diagnosing method has been estimated in a number of studies to at most 50% (see for example C. C. Linneman, 1979, Host-parasite interactions in pertussis, C. R. Manclark and J. C. Hill (ed.) International Symposium on pertussis. US Department of Health, Education and Welfare. Bethesda, Md. pp 3-18).

SEROLOGICAL METHOD

A plurality of serological methods for the diagnosis of whooping-cough exist, all of which are based on the detection of a specific antibody response to the whooping-cough bacterium or to proteins produced by the whooping-cough bacterium. The method which at present is the most sensitive utilizes ELISA (Enzyme-linked immunosorbent assay), the FHA (fimbrial haemagglutinin) produced by the whooping-cough bacterium being used as antigen (M. Granström, G. Granström, A. Lindfors and P. Askelof, 1982. Serologic diagnosis of whooping-cough by an enzyme-linked immunosorbent assay using fimbrial haemagglutinin as antigen. J. Inf. Dis. 146: 741-745).

In this method, sensitivity amounts to 96%, and the method is at present the most sensitive one for the diagnosis of whooping-cough. The method has the disadvantage that in most cases two blood samples are required which are taken at an interval of several weeks to detect a possible increase of the specific antibodies. Such increase of the specific antibodies indicates that an infection is in progress. Although the diagnosis thus is fairly reliable, it usually is too late for a successful treatment of the patient, for example with antibiotics.

It will thus be appreciated that there is considerable need for a method for the diagnosis of whooping-cough, which is highly sensitive and can be carried out in a relatively short time, thereby to prevent the outbreak of epidemics and to enable successful treatment of the patient (for example with antibiotics) at an early stage of the disease.

It is the object of the present invention to provide such a method for the diagnosis of whooping-cough, which is highly sensitive and can be carried out in a relatively short time, and to provide a test kit for carrying the method into effect.

DESCRIPTION OF THE INVENTION

The invention, in one of its aspects, provides an entirely new method for the diagnosis of whooping-cough, said method being carried out by incubating a sample of body fluid (sputum, nasopharyngeal secretion, saliva or blood) from a patient with at least a part of a pertussis toxin-sensitive, chromatophore-containing fish-scale during a predetermined suitable period of time;

subjecting the fish-scale color to a first visual inspection, optionally by means of a microscope;

adding a substance inducing a color change in the fish-scale;

subjecting the fish-scale color to a second visual inspection, optionally by means of a microscope; and comparing the fish-scale color first observed with the subsequently observed fish-scale color, the absence of a color change, or a slight color change, indicating the presence of pertussis toxin in the body fluid sample.

Fish-scales containing chromatophores can change their color. When the pigment granules in the chromatophores are aggregated in the middle of the cell, the scales have a lighter hue than when they are not aggregated. Aggregation can be induced by synthetic means by adding substances inducing a color change in the fish-scale. Pertussis toxin is capable of inhibiting the effect of such substances upon the chromatophores, whereby the expected color change will not be forthcoming, if the chromatophores have previously been subjected to interaction with pertussis toxin.

Practically all fishes are believed to have pertussis toxin-sensitive chromatophore-containing scales. However, it is recommended, for the purpose of the present invention, to select such fish-scales as give a color change which is so distinct that it can be observed by the naked eye. Examples of such fishes are:

Brachyistius frenatus,
Gibbonsia montereyensis,
Hepsopsietta Guttulata,
Holocentrus-sp, and above all Labridae, such as Cuckoo wrasse (Labrus ossifagus),
Ballan wrasse (Labrus berggylta),
Senorita (Oxyjulis californica),
Rock wrasse (Halichoeres semicinctus).

In a preferred embodiment of the method according to the invention, the substance inducing a color change in fish-scales is a catecholamine, for example adrenaline or noradrenaline, and the fish-scale used originates from Labridae, for example cuckoo wrasse (Labrus ossifagus). In the Examples below, use has been made of cuckoo wrasse scales because the chromatophores therein are melanophores providing a highly distinct and rapid color change in the method according to the invention.

The body fluid sample is preferably diluted 20 times with buffer before it is incubated with at least a part of the fish-scale. The diagnostic method according to the invention requires but a small part of a fish-scale, although for practical reasons whole fish-scales will probably be used in actual practice. Incubation temperature and time are not critical. A lower temperature requires a longer incubation time to make the scale change its color. In addition, these two parameters depend upon the scale type utilized. For scale from cuckoo wrasse, an incubation time of 30 min. at a temperature of 37° C. has been found suitable.

The fish-scale color and its change depend upon the specific chromatophores in the scale utilized, and in many cases such a color change is discernible to the naked eye, although in some cases the result will be more reliable if the color and the color change are inspected through a microscope. The microscope may be equipped with a photocell, in which case the change of the color hue can be recorded optoelectrically and thus with objectiveness.

The method for the diagnosis of whooping-cough, according to the present invention, is so far the most sensitive technique and the first to reveal the presence of pertussis toxin in nasopharyngeal secretion and sputum from an infected patient. It has been found that the sensitivity of the method according to the invention for demonstrating pure pertussis toxin lies in the range picogram-femtogram/milliliter, which should be compared to the sensitivity of enzyme-linked immunosorbent assay (ELISA) which is in the range 1-10 nanogram/milliliter.

In a further aspect of the invention, a test kit for the diagnosis of whooping-cough is provided. The kit comprises four separately packaged solutions, viz.

(a) a solution of specific antibodies against pertussis toxin;
(b) a solution of essentially pure pertussis toxin;
(c) a nutrient solution containing at least one pertussis toxin-sensitive chromatophore-containing fish-scale; and
(d) a solution of a substance inducing a color change in the fish-scale type in solution (c).

Solutions (a)–(d) are water-based and may contain conventional additives, such as preservatives, for example sodium azide or methiolate, glycerol to facilitate lowering of the freezing point, and/or buffers, such as Tris buffer och phosphate buffer.

In addition to the above-mentioned solutions (a)–(d), diagnosis naturally requires a body fluid sample from a patient.

Solution (a) of specific antibodies against pertussis toxin is used for checking the specificity, a diluted body fluid sample being preincubated with the specific antibodies against pertussis toxin, which may consist of monoclonal antibodies or a specific antiserum, preferably at 37° C. for 1 h. After incubation, at least a part of a fish-scale from nutrient solution (c) is introduced into the sample. Since the antibodies react with any pertussis toxin that may be present in the sample, the scale color will change from the color first observed to the subsequently observed color.

Solution (b) of an essentially pure pertussis toxin is used for checking that fish-scales from solution (c) have intact chromatophores, solution (d), preferably of noradrenaline, being added to the fish-scale incubated with solution (b) (the pertussis toxin concentration in the solution is, for example, 0.01 ng/ml). If the fish-scale is intact, no color change occurs.

Once it has been established that the fish-scales of solution (c) function, the actual diagnosis is carried out by incubating a body fluid sample from a patient suspected of whooping-cough with at least a part of a fish-scale from solution (c) during a predetermined suitable period of time. Then the scale color is inspected visually, or by means of a microscope, whereupon an adequate amount of solution (d) is added. Finally, the fish-scale color is inspected visually, optionally by means of a microscope, and if no color change between the two visual inspections is forthcoming, this indicates the presence of pertussis toxin in the body fluid sample. If, on the other hand, there is a color change between the first and the second visual inspection, this indicates that there is no pertussis toxin in the body fluid sample, and there is a fair basis for assuming that the patient does not have an ongoing whooping-cough infection.

EXAMPLE 1

This Example accounts for the results of the diagnosis of whooping-cough in sputum samples from patients suspected of whooping-cough. The samples were obtained from Statens Bakteriologiska Laboratorium (the National Swedish Bacteriological Laboratory, SBL), Stockholm, Sweden. The results obtained with the method according to the invention where compared with the results obtained for the same samples by the serological method and the culture method, both carried out by SBL.

Each sputum sample was diluted 20 times with buffer (0.1 ml sample + 1.9 ml phosphate-buffered physiological saline solution containing 1% fetal calf serum, pH = 7.4). At the same time, samples were prepared (from the same serum samples as above) which were preincubated with antiserum containing specific antibodies against pertussis toxin (anti-PTX) for checking the specificity. The antiserum had also been obtained from SBL.

0.2 ml of the diluted samples (triplicate) was incubated with fish-scales from cuckoo wrasse at 37° C. for 30 min., whereupon the scales where placed separately in 0.05 ml buffer on a slide, and the scales where inspected visually and by means of a microscope. The scales appeared to be dark (black) to the naked eye, and the microscope revealed that the melanophores had not aggregated. The scale color was judged by means of a microscope on a five-point scale, according to which 1 = maximum aggregation (aggregated pigments in melanophores) and 5 = maximum dispersion (nonaggregated pigments in melanophores).

Then 0.005 ml $3\times10^{-5}$ M noradrenaline was added to the fish-scales in their buffer solution on the slides. A second inspection of the scale color was made by means of the naked eye and the microscope. The samples containing pertussis toxin remained dark to the naked eye, and the samples containing no pertussis toxin appeared to be of a light hue (grey) to the naked eye. The melanophore aggregation/dispersion was again judged in the manner described above. A color index was calculated for each sample as the difference between the dispersion/aggregation value first judged and the subsequently judged dispersion/aggregation value (i.e. after addition of noradrenaline). Thus, a low value of the calculated color index indicates a high pertussis toxin activity. The results are shown in Table I below.

The fish-scales where checked by adding noradrenaline in accordance with the above technique to fish-scales (triplicate) incubated in buffer only (according to the technique described above) or in buffer containing pure pertussis toxin (0.1 ng/ml).

Besides sputum samples from patients suspected of whooping-cough (samples 1-8), a diagnosis was carried out by the same technique as above on saliva samples from three apparently healthy persons. The results are also accounted for in Table I, the samples being designated A, B and C.

TABLE I

| Sputum sample No. | Colour index | Colour index with anti-PTX | $\Delta$* | Serology | Culture |
|---|---|---|---|---|---|
| 1 | 0.8 ($\pm$0.6) | 3.5 ($\pm$0.5) | 2.7 | — | — |
| 2 | 0.7 ($\pm$1.3) | 3.5 ($\pm$0) | 2.8 | n.d. | n.d. |
| 3 | 0.3 ($\pm$0.3) | 3.8 ($\pm$0.3) | 3.5 | — | + |
| 4 | 0 ($\pm$0) | 4 ($\pm$0) | 4 | + | + |
| 5 | 1.7 ($\pm$0.8) | 3.8 ($\pm$0.3) | 2.1 | + | — |
| 6 | 1.5 ($\pm$1.3) | 3.7 ($\pm$0.3) | 2.2 | + | + |
| 7 | 2 ($\pm$1.3) | 4 ($\pm$0) | 2 | — | — |
| 8 | 2.5 ($\pm$0.7) | 4 ($\pm$0) | 1.5 | — | + |
| A | 3.8 ($\pm$0.3) | 3.7 ($\pm$0.3) | −0.1 | | |
| B | 3.7 ($\pm$1.0) | 3.8 ($\pm$0.3) | 0.1 | | |
| C | 3.5 ($\pm$0.5) | 3.5 ($\pm$0.5) | 0 | | |

*$\Delta$ is the difference between colour index and colour index with anti-PTX.
$\pm$ values indicate standard deviations, and n.d. means that no determination was made.
+ = positive and − = negative.

The above Table I clearly shows that all sputum samples 1-8 from patients suspected of whooping-cough showed pertussis toxin activity, and that all saliva samples A-C from apparently healthy test subjects showed no pertussis toxin activity. Furthermore, it appears that the method according to the invention is more sensitive than both the seriological method and the culture method which are at present commonly used for diagnosis purposes. Sputum samples Nos. 1 and 7 where found, in the method according to the invention, to originate from patients suffering from whooping-cough, although these patients had been deemed free from whooping-cough both by serology and by culture.

EXAMPLE 2

This Example shows the diagnosis of whooping-cough with nasopharyngeal samples from patients suspected of whooping-cough. The samples where obtained from Statens Bakteriologiska Laboratorium (SBL) which provided also the results from serology and culture for these samples.

The nasopharyngeal samples where treated in the same manner as in Example 1. The results are shown in Table 2.

Also the nasopharyngeal sample diagnosis established one case of whooping-cough (sample No. 4) that could not be demonstrated either by serology or culture.

EXAMPLE 3

In this Example, the storage of scale from cuckoo wrasse in nutrient solution was investigated.

Scales from cuckoo wrasse where incubated in tissue culture medium (HAM,sF12 medium+10% fetal calf serum (v/v)+0.5% gentamycin sulphate 0.5% (w/v), about 5 scales/milliliter medium at 4° C. The medium was exchanged every fourth day. The viability of the chromatophores was tested on selected scales at regular intervals by adding noradrenaline to the scales, whereupon the melanophore dispersion/aggregation state (color changes) was judged by means of a microscope. The chromatophores retained their viability in the nutrient medium for three weeks. After that, the chromatophores gradually lost their viability, which became noticeable by the loss of dispersion power in the pigment granules.

This means that fish-scales for the purpose of this invention can be maintained intact for at least 3 weeks, which is an acceptable period of time. The composition of the nutrient solution has as yet not been optimized.

As will appear from this specification, the method according to the invention makes it possible to diagnose whooping-cough much faster than before, and the results are more reliable than those previously obtained by serology and culture.

I claim:

1. A method for the diagnosis of whooping-cough, comprising
   incubating a sample of body fluid from a patient with at least a part of a pertussis toxin-sensitive, chromatophore containing a fish-scale during a predetermined suitable period of time said part of fish containing chromatophores;
   subjecting said fish-scale to a first visual inspection, for color after addition of said sample;

TABLE 2

| Nasopharyngeal sample No. | Colour index | Colour index with anti-PTX | $\Delta$* | Serology | Culture |
|---|---|---|---|---|---|
| 1 | 1.7 ($\pm$1.6) | 4 ($\pm$0.5) | 2.3 | + | + |
| 2 | 0.5 ($\pm$0) | 4 ($\pm$0) | 3.5 | + | — |
| 3 | 1 ($\pm$0.5) | 3.5 ($\pm$0) | 2.5 | + | + |
| 4 | 1.8 ($\pm$1.3) | 4 ($\pm$0) | 2.2 | — | — |
| 5 | 0.7 ($\pm$0.3) | 3.8 ($\pm$0.3) | 3.1 | — | + |

$\Delta$*is the difference between colour index and colour index with anti-PTX.
$\pm$ values indicate standard deviations.
+ =positive and − = negative adding an effective color inducing amount of catecholamine to said fish-scale;

subjecting said fish-scale to a second visual inspection, for color after the addition of catecholamine; and comparing the fish-scale color first observed with the subsequently observed fish-scale color, the absence of a color change, or a slight color change, indicating the presence of pertussis toxin in the body fluid sample.

2. A method as claimed in claim 1, characterized in that the body fluid sample is a sample of nasopharyngeal secretion or sputum.

3. A method as claimed in claim 1, characterized in that the fish-scale is a Labridae scale.

4. A method as claimed in claim 1, characterized in that the catecholamine is noradrenaline, and that the fish-scale is a cuckoo wrasse scale.

5. A test kit for the diagnosis of whooping-cough, characterized in that it comprises the following separately packaged solutions;

(a) a solution of specific antibodies against pertussis toxin;

(b) a solution of essentially pure pertussis toxin;

(c) a nutrient solution containing at least one pertussis toxin-sensitive chromatophore-containing fish-scale; and (d) a solution of a catecholamine.

6. A test kit as claimed in claim 5, characterized in that the fish-scale in solution (c) has been taken from cuckoo wrasse, and that the catecholamine in solution (d) is noradrenaline.

7. The method of claim 1 wherein the visual inspection is by means of a microscope.

* * * * *